United States Patent [19]

Sanders

[11] Patent Number: 4,858,617

[45] Date of Patent: Aug. 22, 1989

[54] CARDIAC PROBE ENABLING USE OF PERSONAL COMPUTER FOR MONITORING HEART ACTIVITY OR THE LIKE

[75] Inventor: William J. Sanders, Palo Alto, Calif.

[73] Assignee: ITH, Inc., San Jose, Calif.

[21] Appl. No.: 95,314

[22] Filed: Sep. 10, 1987

[51] Int. Cl.$^4$ .............................................. A61B 5/04
[52] U.S. Cl. ................................... 128/696; 128/710; 128/712; 128/731
[58] Field of Search ............... 128/640, 696, 710, 712, 128/731, 732; 364/417

[56] References Cited

U.S. PATENT DOCUMENTS

| | | | |
|---|---|---|---|
| 3,222,755 | 12/1965 | Grass | 29/155.5 |
| 3,650,264 | 3/1972 | Janssen | 128/2.06 A |
| 3,830,227 | 8/1974 | Green | 128/2.06 R |
| 3,830,228 | 8/1974 | Foner | 128/2.06 R |
| 4,013,068 | 3/1977 | Settle et al. | 128/732 |
| 4,109,648 | 8/1978 | Larke et al. | 128/2.06 E |
| 4,364,397 | 12/1982 | Citron et al. | 128/710 |
| 4,417,590 | 11/1983 | Smith et al. | 128/731 |
| 4,519,398 | 5/1985 | Lisiecki et al. | 128/710 |
| 4,583,549 | 4/1986 | Manoli | 128/640 |
| 4,606,352 | 8/1986 | Geddes et al. | 128/712 |
| 4,624,263 | 11/1986 | Slavin | 128/710 |

FOREIGN PATENT DOCUMENTS 1907378 9/1969 Fed. Rep. of Germany ...... 128/639

OTHER PUBLICATIONS

Makoto Takagi, "The Electrodes-Triangle" (Date not known), Annotations, pp. 427-428.

Primary Examiner—Leo P. Picard
Attorney, Agent, or Firm—Phillips, Moore, Lempio & Finely

[57] ABSTRACT

A compact and economical probe unit has projecting electrodes for sensing minute voltage variations at spaced apart locations on a persons skin or other surface. Internal circuits generate serial form digital signals indicative of the voltage variations for transmission to a personal computer where an electrocardiogram or other data presentation may be displayed. The probe includes a digital type of optical isolator through which the serial signals are transmitted, the output circuit of the isolator being energized by voltage taken from the computer and the input circuit being independently energized from a battery within the probe and thus there is no electrically conductive path between the computer and the electrodes. Among other uses, the probe enables unskilled persons to monitor their own heart activity as it is economical, safe and easily operated and makes use of a common computer for display rather than a costly electrocardiograph.

8 Claims, 13 Drawing Sheets

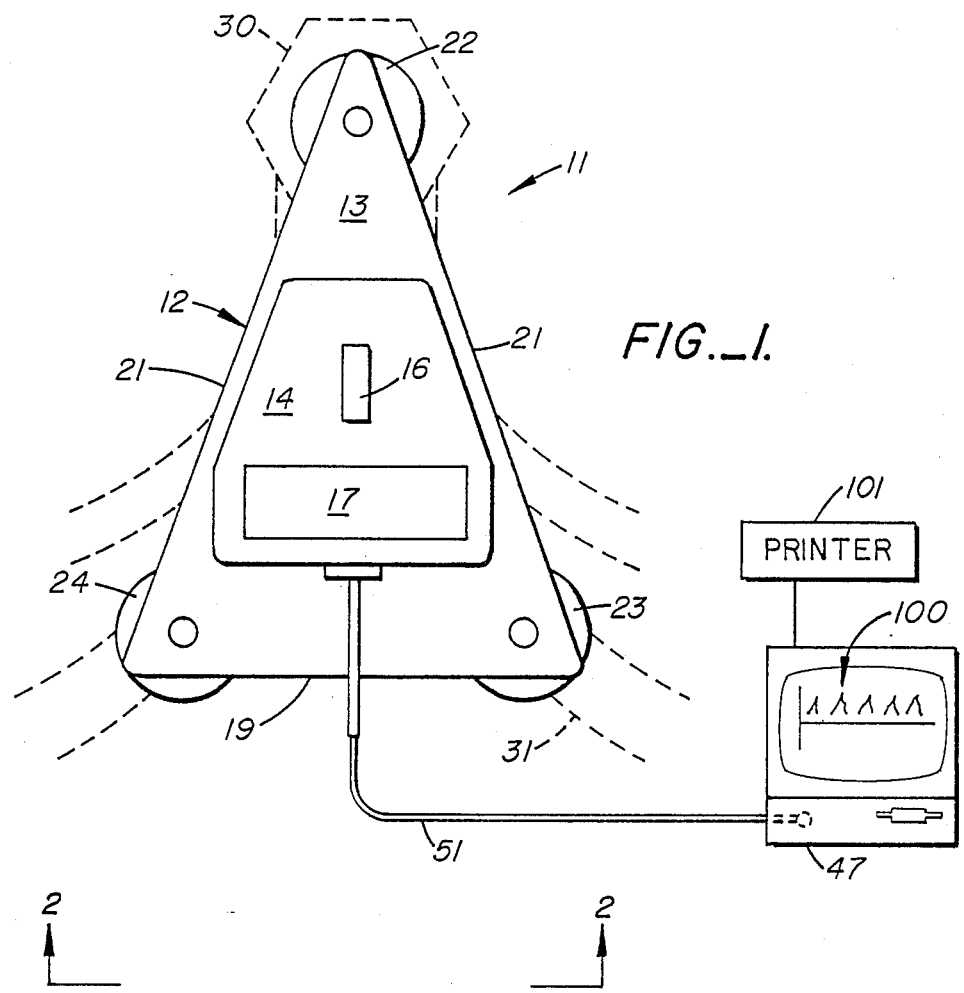
FIG._1.
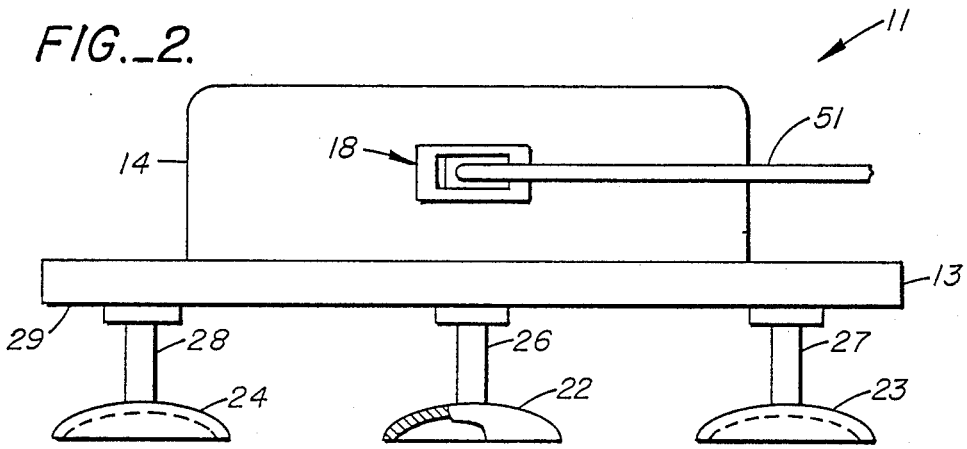
FIG._2.

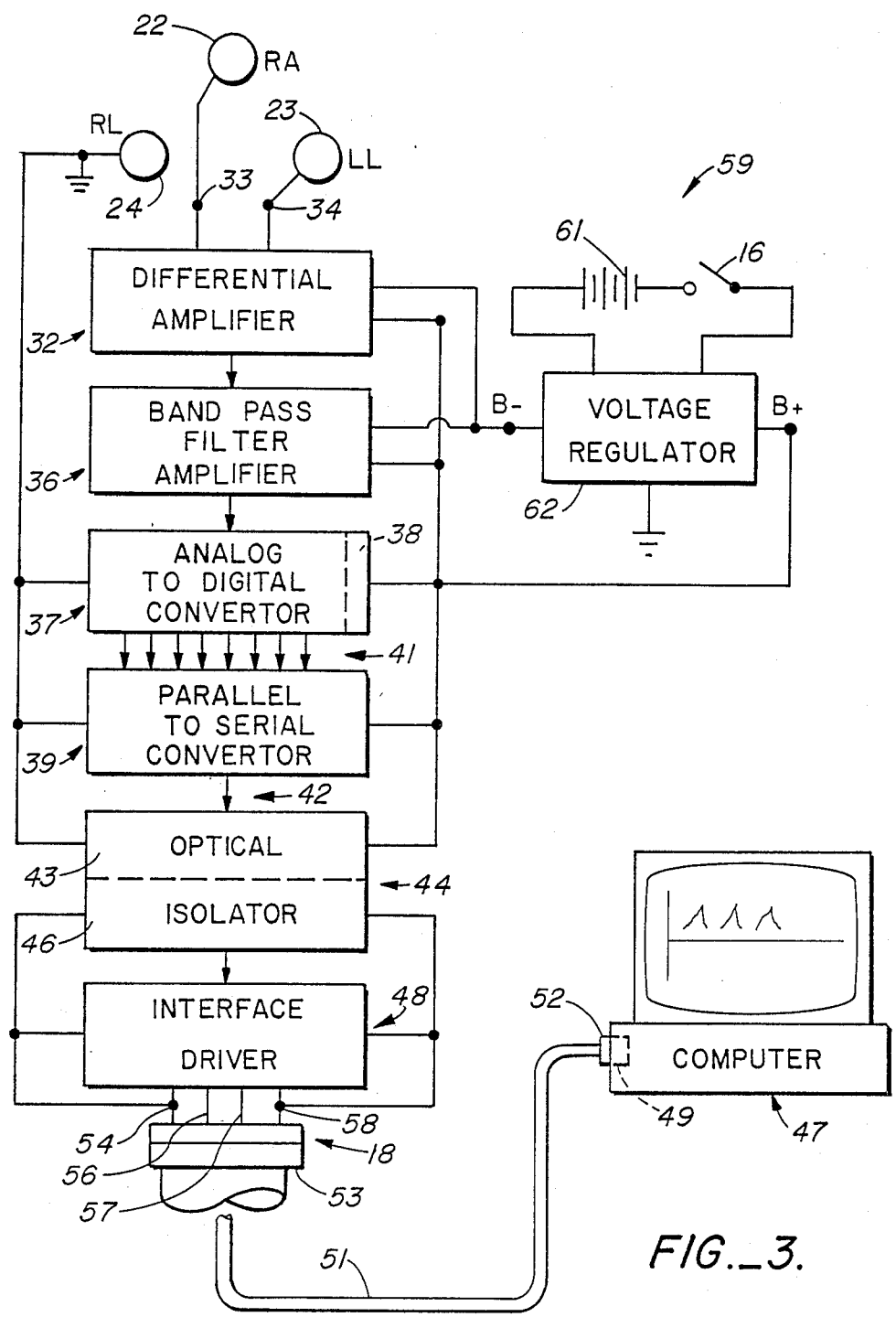
FIG._3.

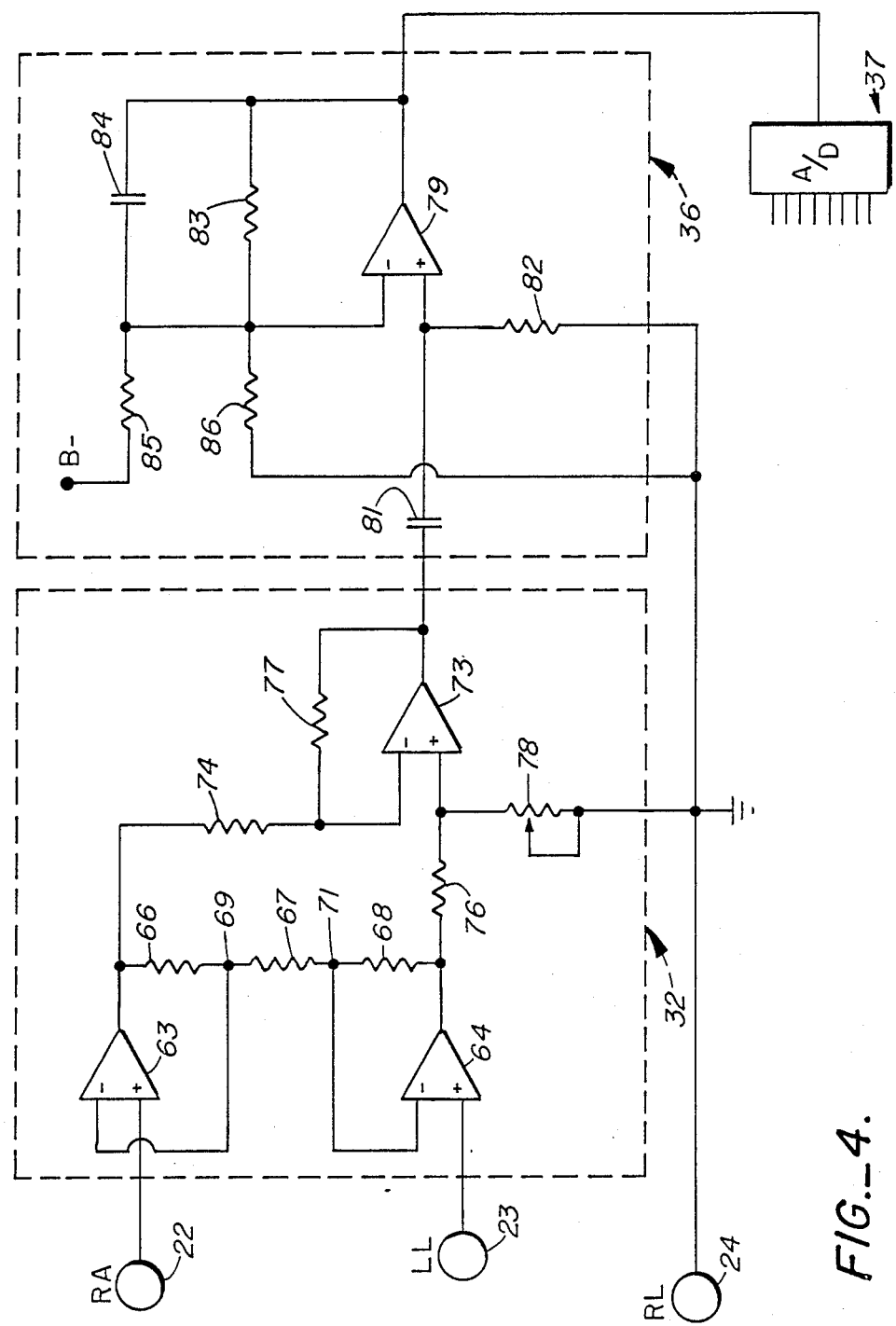
FIG._4.

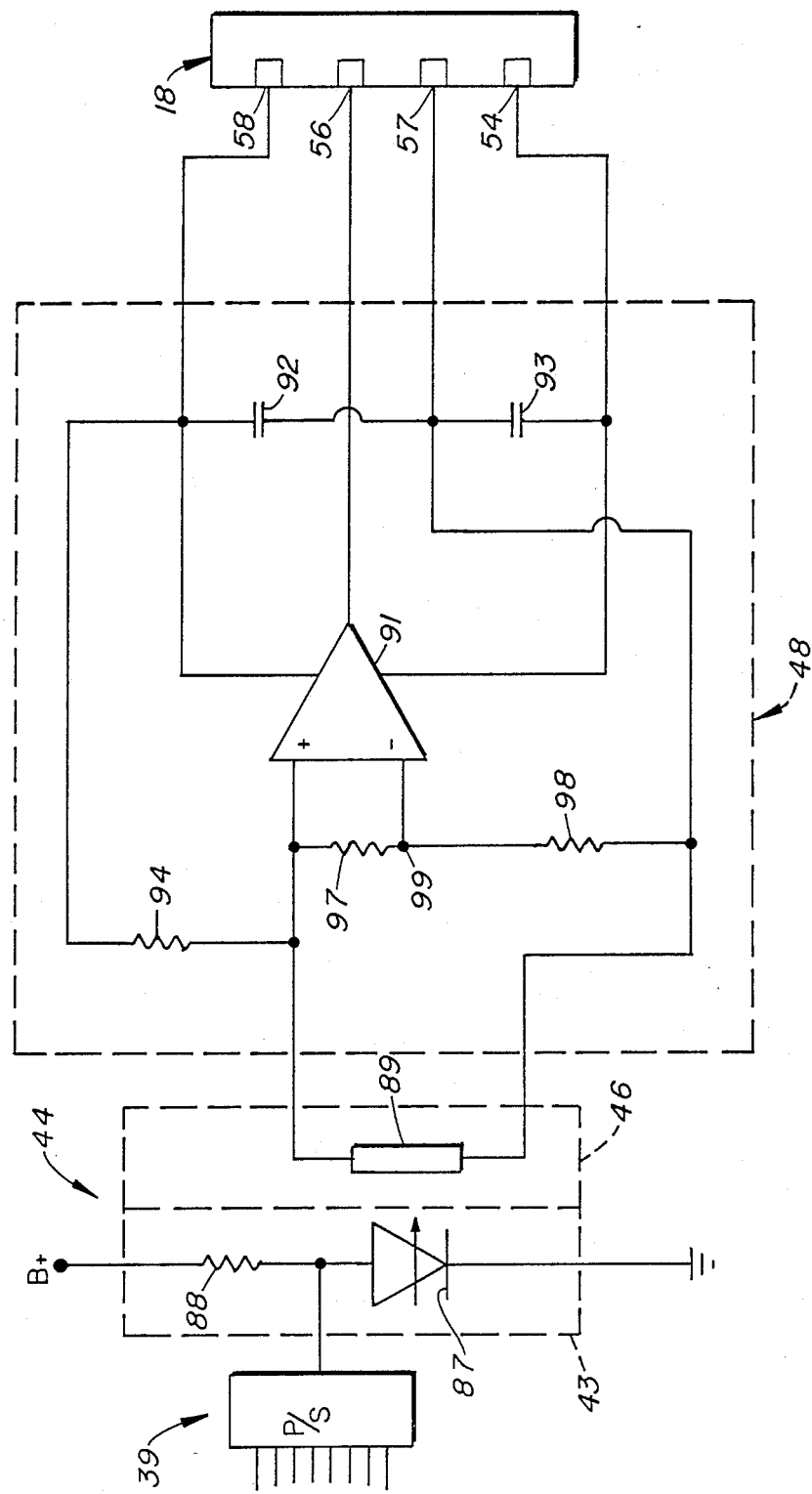
FIG._5.

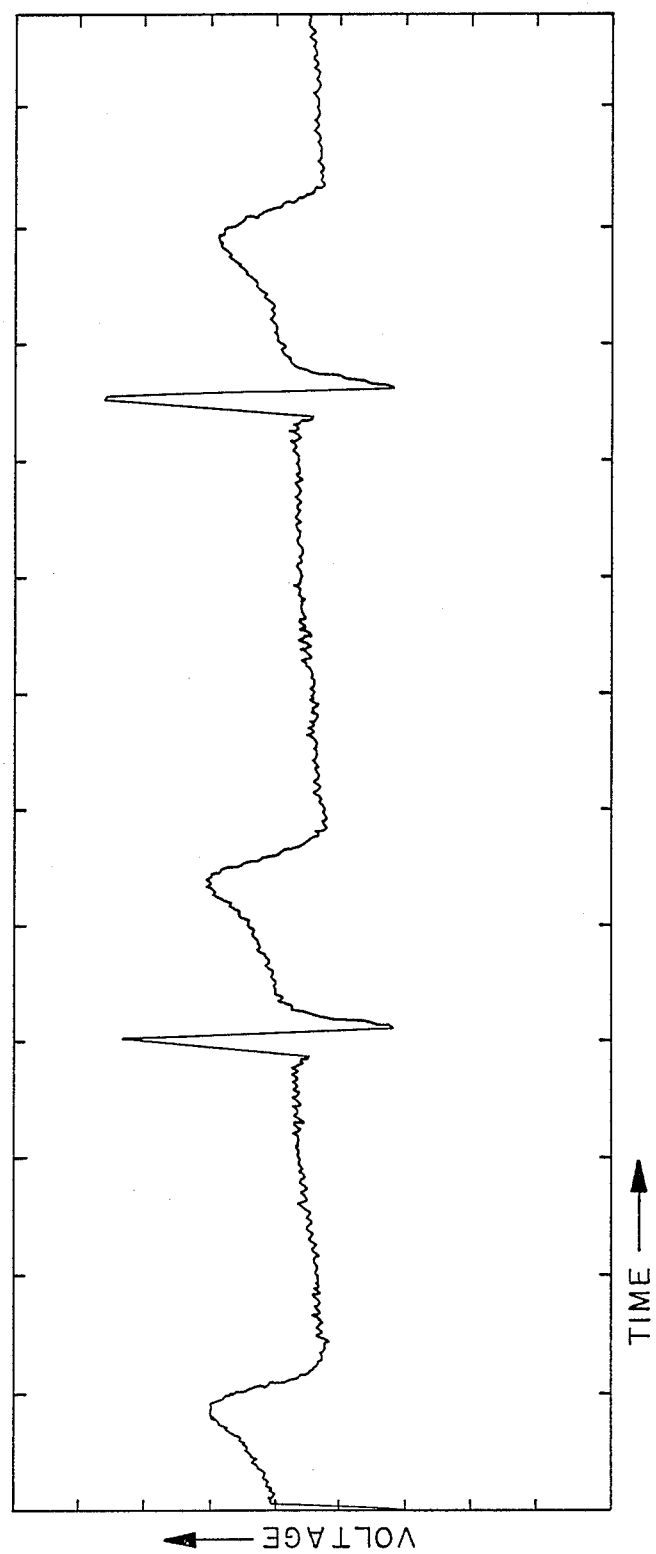
FIG._6.

CARDIAC PROBE ENABLING USE OF PERSONAL COMPUTER FOR MONITORING HEART ACTIVITY OR THE LIKE

TECHNICAL FIELD

This invention relates to instruments for producing electrocardiograms or the like and more particularly to a compact and economical probe which enables display of such data at the screen of a personal computer.

BACKGROUND OF THE INVENTION

Electrocardiographs which visually display the heart activity of living subjects are well recongized to be of great value in the diagnosis and treatment of medical patients. Instruments of this type are also useful for a number of other purposes such as in the monitoring of cardiac activity in persons undergoing exercise training or for the display of an ECG for educational purposes.

The conventional electrocardiograph is a complex, costly and usually bulky assembly which must be operated by professional medical personnel or highly skilled technicians. Consequently, usage of such equipment has more or less been restricted to hospitals, medical clinics, and medicial emergency vehicles. Compact and economical cardiac monitors have been developed but in general these produce only an audible signal or otherwise do not provide the type of data that is available from an ECG.

A more compact and economical cardiac monitor would be highly advantageous not only in medical facilities but also for usage elsewhere. Such a device would for example, enable persons with cardiovascular problems to monitor their heart activity in their homes. Such apparatus should not require that the operator have specialized skills or undergo extensive training and should not expose the user to potential hazards such as electrical shock.

Instruments for obtaining electrodcardiograms include spaced apart electrodes which contact the persons skin in the thoracic region in order to sense the minute voltage changes which accompany heart activity. The sensed voltage changes are amplified and displayed on the screen of an oscilloscope and/or are applied to a chart recorder to printer type of readout device to provide the electrocardiogram. The sensed voltage signals have also heretofore been digitized and transmitted to a computer which may variously be programmed to detect abnormal activity, to determine average values for specific phases of the cyclic heart activity or to analyze the data in a variety of other ways.

Prior computer aided heart monitoring systems do not resolve the problems discussed above. The computer typically functions only as a permanent component of the electrocardiograph and is not used for any other purpose. Thus it further increases the cost and often the bulk of the heart activity monitoring installation. The prior computer aided systems, like older types of electrocardiograph, require highly trained operators.

The present invention is directed to overcoming one or more of the problems discussed above.

SUMMARY OF THE INVENTION

In one aspect, the present invention provides a probe for producing and transmitting digital signals indicative of heart activity or the like to a digital computer. The probe includes a housing member having signal output means for transmitting serial form digital signals to the computer and first, second and third electrodes extend outward from a surface of the housing member, the electrodes being mutually spaced apart. The housing member includes first circuit means for producing a first analog signal which varies in accordance with variations of the electrical potential at the first electrode relative to the electrical potential at the third electrode and second circuit means for producing a second analog signal which varies in accordance with variations of the electrical potential at the second electrode relative to the potential at the third electrode. Third circuit means produce a third analog signal which varies in accordance with variations of the difference beetween the first and second analog signals. The probe member further includes digital circuit means for converting the third analog signal to sequences of serial form digital signals and for transmitting the serial for digital signals to the output means.

In another aspect of the invention, an optical isolator is coupled between the digital circuit means and the output means. The output side of the optical isolator is energized by voltage obtained from the computer data input port while the input side of the optical isolator and the first, second and third circuit means are energized by an independent direct current source disposed within the housing member.

In still another aspect, the invention provides a probe for detecting voltage variations between spaced apart locations on a surface and for transmitting digital signals indicative of the voltage variations to a digital computer. The probe has a housing member with a signal output port for connection to the computer and has first, second and third mutually spaced apart electrodes which extend outward from the housing for contact with the surface. First circuit means produce a first analog signal indicative of voltage at the first electrode relative to the voltage at the third electrode and second circuit means produce a second analog signal indicative of the voltage at the second electrode relative to the voltage at the third electrode. Third circuit means produce a third analog signal indictative of the difference between the first and second analog signals. Fourth circuit means convert the third analog signal into parallel form digital signals and fifth circuit means convert the parallel form digital signals into serial form digital signals. An optical isolator at the probe is coupled between the fifth circuit means and the output port to transmit the serial form digital signals to the port.

The invention provides a compact and economical instrument which enable minute voltage variations between spaced apart areas of a surface, such as the human skin, to be sensed and converted into serial form digital signals which may be applied to a personal computer to provide a visual display indicative of the voltage variations at the monitor screen of the computer. Among other uses, the invention enables unskilled persons to monitor their own heart activity away from medical facilities as the construction can be inexpensive, safe and easy to operate and connects to a commonly available display, a personal computer, rather than to a specialized electrocardiograph.

BRIEF DESCRIPTION OF THE DRAWINGS

FIG. 1 depicts a cardiac activity probe and an associated computer in accordance with a preferred embodiment of of the invention.

FIG. 2 is an end view of the cardiac activity probe of FIG. 1 taken along line II—II thereof.

FIG. 3 is a schematic circuit diagram of electronic components of the probe of the preceding figures.

FIG. 4 is a detailed circuit diagram of the differential amplifier and band pass filter amplifier components of the probe which are shown in block form in FIG. 3.

FIG. 5 is a detailed circuit diagram of the optical isolator and interface driver circuits shown in block form in FIG. 3.

FIGS. 6 through 11 describes a detailed computer program for enabling computer graphic display of data produced by the probe of the preceding figures.

FIG. 12 describes another suitable computer program for displaying data transmitted to a computer by the probe.

FIG. 13 depicts a print out of an ECG from data produced by the probe.

DETAILED DESCRIPTION OF THE PREFERRED EMBODIMENT

Referring initially to FIGS. 1 and 2 of the drawings in conjunction, a cardiac probe unit 11 in accordance with this particular embodiment of the invention has a housing member 12 which includes a triangular plate portion 13 and a thicker housing 14 at one surface of the plate. The housing 14 contains electronic components which will hereinafter be described. Externally visible components of the housing 14 include a manually operable on-off switch 16, an openable battery compartment lid 17 and a signal output port 18.

Plate portion 13 defines an isosceles triangle with a base 19 that is shorter than the sides 21. First, second and third electrodes, 22, 23 and 24 respectively, are situated at the ends of conductive support posts, 26, 27, and 28 respectively, which extend outward from the surface 29 of plate 13 that is opposite from housing 14. First electrode 22 is located at the apex of the triangular plate 13 at which sides 21 converge. Second electrode 23 is at the right hand side of base 19 when the probe 11 is in the operating orientation shown in the drawings and third electrode 24 is at the left side of the base.

In keeping with the common terminology in the art, the first, second and third electrodes 22, 23, 24 may be hereinafter referred to respectively as the right arm electrode, the left leg electrode and the right leg electrode. This does not mean that the electrodes 22, 23, 24 contact those particular portions of the human body during use. The triangular plate 13 is proportioned to fit over the frontal thoracial region of the human body with the right arm electrode 22 being over the sternum 30, left leg electrode 23 being over the lower ribs 31 at the left side of the body and right leg electrode being over the lower ribs at the right side of the body.

Positioning of the electrodes 22, 23, 24 over bony regions of the body allows firmer pressure to be exerted and reduces artifact in the signals due to electrode movement. Such placement also reduces signal degradation from non-cardial muscle activity.

The spacing of the electrodes 22, 23, 24 from plate 13 by support posts 22, 23, 24 enables firm contact of the electrodes with the skin by accomodating to the convexity of the human chest. The triangular configuration of the probe 11 is particularly useful for women as it avoids the areas of the breasts.

Each electrode 22, 23, 24 preferably has a concave contact surface 32 and thus is essentially cup shaped. Pressure is then concentrated at a circle on the skin and this reduces electrical resistance and also reduces effects from body hair.

Referring now to FIG. 3, electronic components of the probe 11 include a first circuit stage 32 which is a low gain differential amplifier of the type having high common mode rejection. The first stage 32 has inputs 33 and 34 connected to the right arm electrode 22 and left leg electrode 23 respectively. The right leg electrode 24 in effect constitutes a chassis ground for the first stage 32 and certain other components of the probe 11 as will hereinafter be described in more detail.

First stage 32 produces a first analog signal indicative of voltage variations at right arm electrode 22 relative to the voltage at right leg electrode 24 and also produces a second analog signal indicative of voltage variations at left leg electrode 23 relative to the voltage at the right leg electrode and transmits a third analog signal indicative of the difference between the first and second analog signals to a second circuit stage 36. Sensing the voltage at electrodes 22 and 23 relative to the voltage at electrode 24 rejects the effects of electrical artifacts, such as charges produced by nearby electrical equipment, which can appear on the body surface with a much larger amplitude than ECG signals.

The second circuit stage 36 is a band pass amplifier which eliminates direct current and low frequency components of the third analog signal to eliminate base line drift and which also eliminates high frequency components to further reduce electrical artifact such as residual power line signals and signals generated by surface muscle activity. Stage 36 may typically be configured to transmit only frequencies in the range from about 0.5 Hz to about 25 Hz. In this specific embodiment, the band pass amplifer 36 also shifts the signal amplitude from +/− one volt to 2.5 volts +/− one volt to accomodate to the input signal acceptance range of this particular third circuit stage 37.

The third circuit stage 37 is an analog to digital signal convertor which may be of known construction and recieves the third analog signal from circuit stage 36. The clock circuit 38 of this particular analog to digital convertor 37 causes sampling of the third analog signal at a frequency of 250 Hz and transmits an eight bit digital output signal in parallel form at each such sampling.

The fourth circuit stage 39 is a parallel to serial digital signal convertor which may also be of known construction. Convertor 39 converts the parallel eight bit signals received simultaneously on eight input lines 41 into sequential bit signals which can be transmitted on a single output line 42. The output signalling rate in this particular embodiment is 9,600 bits per second.

The serial form signals from circuit stage 39 are transmitted to the input circuit 43 of an optical isolator or coupler 44 which may also be of known internal construction. The input circuit 43 converts the serial signal bits from electrical to optical form and the output circuit 46 of the isolator reconverts the optical signals back to electrical signal bits. This electrically isolates the electrodes 22, 23, and 24 from the computer 47 to which the probe 11 is coupled thereby eliminating any risk of electrical shock as there is no electrically conductive path between such components.

Digitizing and serializing of the signals within the probe 11 prior to transmission of the signals through optical isolator 44 contributes substantially to the objective of providing an inexpensive monitoring device. Digital optical isolators 44 and particularly single channel isolators are less costly than analog isolators which must sensitively respond to slight differences in signal voltage rather than to two distinctly different voltage levels as in the case of digital isolators.

The sequence of serial signals from optical isolator 44 is transmitted to the output port 18 of probe unit 11 through a computer interface driver circuit 48 within the the probe 11. Circuit 48 operates as an amplifier and level shifter which converts the signal voltages into the standardized range required for the serial input ports 49 of personal computers 47.

A four conductor cable 51 provides for coupling of the probe 11 output port 18 with the serial port 49 which is present on personal computers 47 for the purpose of receiving digital signals in serial form from an external source. Cable 51 has a connector 52 at one end compatible with the serial port 49 of the particular brand of computer 49 and has a connector 53 at the other end that is engagable with probe port 18 and which connect each of the standard four pins (not shown) of the computer serial port 49 with a separate one of four contacts 54, 56, 57 and 58 of probe port 18. The probe port 18, mating connector 53 and cable 51 may, if desired, be of the low cost type used for telephone receiver installations as four conductors are used in each case.

Cable 51 connects contacts 56 and 57 with the "receive data" and "signal ground" pins, respectively of the computer serial port 49 and connects contacts 54 and 58 with the "terminal ready" and "transmit data" pins, respectively, of the computer port. Output signals from the interface driver 48 are transmitted to the computer 47 through contact 56 with contact 57 being the signal ground conductor.

It is a characteristic of standard personal computer serial ports 49 that a D.C. voltage of +5 volts is present on the "terminal ready" pin during operation and a D.C. voltage of −5 volts is present at the "transmit data" pin when it is not transmitting. These voltages are used to provide operating power for the interface driver 48 and ouput circuit 46 of the optical isolator of the present invention by connecting the power terminals of such circuits 48 and 46 across contacts 54 and 58.

The input circuit 43 of optical isolator 44 and circuit stages 36, 37, 38, and 39 are provided with an independent D.C. power source 59. In particular, the probe 11 includes a battery 61 connected to a voltage regulator 62 in series with the probe on-off switch 16. Regulator 62 has positive and negative outputs B+ and B− which apply operating power, at constant voltages relative to the chassis ground defined by right leg electrode 24, to circuit stages 32 and 36. Only positive voltage from terminal B+ is applied to stages 37 and 39 and isolator input circuit 43 which do not require bipolar power in this embodiment.

Use of D.C. voltage derived from the computer 47 for operating the interface driver 48 and output circuit 46 of optical isolator 43 while the other components of the probe 11 operate from an independent self-contained power supply 59 results in there being no electrically conductive path between the computer 47 and the electrodes 22, 23, 24. Thus the computer 47 is not a source of possible electrical shock and cant transmit signal artifact to the electrodes.

FIG. 4 depicts suitable circuit detail for the first and second circuit stages 32 and 36. In particular, right leg electrode 22 and left leg electrode 23 are connected to the non-inverting inputs of a first pair of amplifiers 63 and 64 respectively which amplify the minute voltages that are sensed by the electrodes. The output of amplifier 63 is connected to the output of amplifier 64 through three series connected resistors 66, 67 and 68. The circuit junction 69 between resistors 66 and 67 is connected to the inverting input of amplifier 63 and the circuit junction 71 between resistors 67 and 68 connects to the inverting input of amplifier 64.

The amplified voltage signals from amplifiers 63 and 64 are respectively applied to the inverting and non-inverting inputs of a differential amplifier 73 through input resistors 74 and 76 respectively. A feedback resistance 77 is connected across the inverting input and output of amplifier 73 and an adjustable resistance 78 is connected between the non-inverting input and ground. Resistance 78 may be adjusted to compensate for offset amplifier 73 and to null any common mode output.

The first and second analog signal voltages produced by amplifiers 63 and 64 are proportional to the voltages sensed by electrodes 22 and 23 respectively at any given time. Differential amplifier 73 produces a third analog signal voltage which varies in accordance with variations of the difference between the first and second analog signals.

The second circuit stage 36 or band pass filter amplifier may include another amplifier 79 having a non-inverting input coupled to the output of the differential amplifier 73 through a capacitor 81 and which is also connected ground through a resistor 82. Capacitor 81 and resistor 82 form a high pass filter which blocks direct current and supresses low frequency signal variations.

Another resistor 83 and capacitor 84 are connected in parallel across the inverting input and output of amplifier 79 and function as a high pass filter which eliminates high frequency artifact from the signal. An additional resistor 86 connected between the inverting input and ground operates in conjunction with resistor 83 to establish the gain of the amplifier 79 to provide a signal voltage range compatible with the particular analog to digital convertor 37 to which the amplifier is coupled. Resistor 85 which connects in the inverting input to B− provides offset.

Referring now to FIG.5, the input circuit 43 of optical isolator 44 has a light emitting diode 87 connected between the power source terminal B+ and ground in series with a resistor 88 and receives the serial form digital signals from parallel to serial signal convertor 39 at the circuit junction between the diode and resistor. The output circuit 46 of isolator 44 includes a photosensitive transistor 89 of the type which exhibits a variable gain in response to changes in the light output of diode 87 produced by the incoming signals.

The interface driver 48 may have still another amplifier 91 which has an output connected to the receive data contact 56 of the probe output port 18. The positive and negative power inputs of amplifier 91 are respectively connected to the transmit data contact 58 and terminal ready contact 54 of the output port 18 to supply operating voltage derived from the computer. A capacitor 92 is connected across contacts 57 and 58 and another capacitor 93 is connected across contacts 54 and 57 to provide energy storage for the relatively high impedance power supply formed by transmit data and data terminal ready pins of the computer port.

The photosensitive transistor 89 of optical isolator 44 is connected across contacts 57 and 58 in series with a fixed resistor 94. The non-inverting input of amplifier 91 connects to the circuit junction 96 between resistor 94 and photosensitive transistor 89 and also connects to ground contact 57 through a pair of series resistors 97 and 98. The inverting input of the amplifier 91 connects to the circuit junction 99 between resistors 97 and 98.

Amplifier 91 in conjunction with resistors 97 and 98 acts as a comparator which converts the voltage variations across photosensitive transistor 89 to a voltage range that is compatible with the computer, for example to +/−5 volts for the EIA RS-232 format.

Referring again to FIG. 1, the signals transmitted to computer 47 may variously be utilized to provide a graphical display 100 of successive voltage fluctuations indicative of heart activity and/or to provide a print out of an ECG at a printer 101 coupled to the computer or for other purposes. The data may, if desired, be stored on a disc by the computer 47.

FIGS. 6 through 11 describe a suitable detailed program for enabling computer graphic display of data produced by the probe. FIG. 12 describes an alternate program which may also be used for the purpose.

The invention has been herein described with respect to the monitoring of heart activity but can also be used for monitoring voltage variations between spaced areas on a surface in other contexts.

While the invention has been described with respect to a single preferred embodiment for purposes of example, many variations in the construction are possible and it is not intended to limit the invention except as defined in the following claims.

I claim:

1. A unitary probe for producing and transmitting computer compatible serial form digital signals indicative of heart activity of a subject to a spaced apart digital computer of the general purpose type at which software may be changed by the operator to run any of a variety of different computer programs and which has a serial data input port, comprising:
    a probe housing having a configuration adapted for disposition at the thoracic region of said subject and having signal output means for transmitting said digital signals to said serial data input port of said computer,
    first, second and third electrodes secured to said housing and extending outward from a surface thereof, said electrodes being mutually spaced apart,
    first circuit means for producing a first analog signal which varies in accordance with variations of the electrical potential at said first electrode relative to the electrical potential at said third electrode.
    second circuit means for producing a second analog signal which varies in accordance with variations of the electrical potential at said second electrode relative to the electrical potential at said third electrode.
    third circuit means for producing a third analog signal which varies in accordance with variations of the difference between said first and second analog signals,
    signal conversion circuit means for converting said third analog signal to sequences of serial form digital signal bits,
    each of said circuit means being within said probe housing,
    an electrical power supply disposed within said probe housing and being coupled to each of said circuit means to supply operating current thereto, and
    isolating means for transmitting said sequences of signal bits to said serial data input port of said computer through said output means of said probe housing and which converts said signal bits to nonelectrical form and then back into electrical form to electrically isolate said subject from said computer.

2. The probe of claim 1 wherein said isolation means includes an optical isolator coupled between said signal conversion circuit means and said output means.

3. The probe of claim 2 wherein said optical isolator has an electrically energized signal input circuit in which said signal bits are converted from electrical form to optical form and has an electrically energized signal output circuit in which said signal bits are converted back to electrical form and wherein said serial data input port of said computer includes a conductor having a direct current voltage thereon, further comprising:
    means for energizing said output circuit of said optical isolator from said conductor of said serial data input port of said computer, and
    means for independently energizing said input circuit of said optical isolator from said electrical power supply.

4. The probe of claim 1 wherein said signal conversion circuit means includes:
    an analog to digital signal convertor having a signal input coupled to said third circuit means for receiving said third analog signal therefrom and having a signal output for transmitting a corresponding signal in parallel digital form,
    a parallel to serial digital signal convertor having signal inputs coupled to said output of said analog to digital signal convertor for receiving said parallel form signal therefrom and having an output for transmitting said signal in serial form.

5. The probe of claim 4 wherein said isolating means includes an optical isolator coupled between said output of said parallel to serial signal convertor and said output means of said probe housing.

6. The probe of claim 5 further including a computer interface driver circuit located in said probe housing said optical isolator being coupled to said output means through said interface driver circuit.

7. The probe of claim 1 wherein said probe housing has a substantially isosceles triangle configuration with sides that are longer than the base, said second and third electrodes being situated at the apexes which are at said base and said first electrode being situated at the apex which is remote from said base.

8. A unitary probe for detecting voltage variations at the thoracic region of a subject and for transmitting computer compatible serial form digital signals indicative of said voltage variations to a spaced apart general purpose digital computer of the type at which programming can be changed by the operator and which has a serial data input port, said serial data input port having a conductor at which a direct current voltage is present, comprising:
    a probe housing having a configuration adapted for emplacement of said housing at said thoracic region of said subject and having a signal output port for connection to said serial data input port of said computer,
    first, second and third mutually spaced apart electrodes extending outward from said probe housing for contact with said surface, first circuit means for producing a first analog signal indicative of voltage at said first electrode relative to the voltage at said third electrode,
second circuit means for producing a second analog signal indicative of voltage at said second electrode relative to the voltage at said third electrode.
third circuit means for producing a third analog signal indicative of the difference between said first and second analog signals,
fourth circuit means for converting said third analog signal into parallel form digital signals,
fifth circuit means for converting said parallel form digital signals into serial form digital signals,
each of said circuit means being disposed within said probe housing,
an optical isolator within said probe housing, said optical isolator having an input side coupled to said fifth circuit means to receive said serial form digital signals and having an output side for transmitting said serial form digital signals,
a computer interface driver disposed within said probe housing and being coupled between said output side of said optical isolator and said signal output port of said probe housing to transmit said serial form digital signals thereto,
a direct current power supply disposed in said probe housing and being coupled to each of said circuit means and to said input side of said optical isolator to supply operating current thereto, and
means for connecting said conductor of said computer serial data port to said output side of said optical isolator and to said interface driver to supply operating current thereto.

* * * * *